(12) United States Patent
Edwards

(10) Patent No.: US 6,517,535 B2
(45) Date of Patent: *Feb. 11, 2003

(54) APPARATUS FOR ABLATING TURBINATES

(75) Inventor: Stuart D. Edwards, Portola Valley, CA (US)

(73) Assignee: Gyrus ENT L.L.C., Bartlett, TN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/437,306

(22) Filed: Nov. 9, 1999

(65) Prior Publication Data

US 2002/0091381 A1 Jul. 11, 2002

Related U.S. Application Data

(63) Continuation of application No. 08/753,063, filed on Nov. 19, 1996, now abandoned, which is a continuation-in-part of application No. 08/754,588, filed on Nov. 19, 1996, now Pat. No. 5,746,224, and a continuation-in-part of application No. 08/752,076, filed on Nov. 19, 1996, now Pat. No. 5,800,429, which is a continuation-in-part of application No. 08/651,796, filed on May 22, 1996, now abandoned, which is a continuation-in-part of application No. 08/651,798, filed on May 22, 1996, now abandoned, which is a continuation-in-part of application No. 08/265,459, filed on Jun. 24, 1994, now Pat. No. 5,505,730.

(51) Int. Cl.[7] .............................................. A61B 18/18
(52) U.S. Cl. .......................... 606/41; 607/101; 128/898
(58) Field of Search .............................. 606/27–31, 41, 606/42, 45–50; 607/100–105, 99, 115, 116; 604/114

(56) References Cited

U.S. PATENT DOCUMENTS

| 1,798,902 A | 3/1931 | Raney |
| 3,901,241 A | 8/1975 | Allen, Jr. |
| 4,011,872 A | 3/1977 | Komiya |

(List continued on next page.)

FOREIGN PATENT DOCUMENTS

DE          43 03 882 A      2/1995

(List continued on next page.)

OTHER PUBLICATIONS

Kaneko, et al., *Physiological Laryngeal Pacemaker*, May 1985, Trans Am Soc Artif Intern Organs, vol. XXXI, pp. 293–296.

(List continued on next page.)

*Primary Examiner*—Michael Peffley
(74) *Attorney, Agent, or Firm*—Heller Ehrman White & McAliffe; Paul Davis

(57) ABSTRACT

An apparatus is provided for ablating at least a portion of a nasal concha. By ablating at least a portion of a nasal concha, the size of the nasal concha is reduced. The three nasal concha in the body (inferior, middle and superior nasal concha) form at least a portion of the three nasal meatus (inferior, middle and superior nasal meatus) in the body. By reducing the size of a nasal concha, obstruction of a nasal meatus is reduced or eliminated. As a result, air flow through the nasal meatus is improved. In one embodiment, the apparatus includes a catheter having a distal portion with a dimension configured for positioning the catheter distal portion through a nostril of a patient into a nasal meatus at a surface of a nasal concha, an expandable member positioned adjacent the catheter distal portion, an energy delivery device for delivering ablative energy positioned adjacent the catheter distal portion, and a lumen coupled to the catheter for delivering a medium into the expandable member to expand the expandable member.

10 Claims, 14 Drawing Sheets

U.S. PATENT DOCUMENTS

| | | |
|---|---|---|
| 4,196,724 A | 4/1980 | Wirt et al. |
| 4,411,266 A | 10/1983 | Cosman |
| 4,423,812 A | 1/1984 | Sato |
| 4,532,924 A | 8/1985 | Auth et al. |
| 4,565,200 A | 1/1986 | Cosman |
| 4,901,737 A | 2/1990 | Toone |
| 4,906,203 A | 3/1990 | Margrave et al. |
| 4,907,589 A | 3/1990 | Cosman |
| 4,943,290 A | 7/1990 | Rexroth et al. |
| 4,947,842 A | 8/1990 | Marchosky et al. |
| 4,966,597 A | 10/1990 | Cosman |
| 4,976,711 A | 12/1990 | Parins et al. |
| 5,046,512 A | 9/1991 | Murchie |
| 5,047,028 A * | 9/1991 | Qian .......................... 606/49 |
| 5,057,107 A | 10/1991 | Parins et al. |
| 5,078,717 A | 1/1992 | Parins et al. |
| 5,083,565 A | 1/1992 | Parins |
| 5,094,233 A | 3/1992 | Brennan |
| 5,100,423 A | 3/1992 | Fearnot |
| 5,122,137 A | 6/1992 | Lennox |
| 5,125,928 A | 6/1992 | Parins et al. |
| 5,190,541 A | 3/1993 | Abele et al. |
| 5,197,963 A | 3/1993 | Parins |
| 5,197,964 A | 3/1993 | Parins |
| 5,215,103 A | 6/1993 | Desai |
| 5,256,138 A | 10/1993 | Burek et al. |
| 5,257,451 A | 11/1993 | Edwards et al. |
| 5,275,162 A | 1/1994 | Edwards et al. |
| 5,277,201 A | 1/1994 | Stern |
| 5,281,216 A | 1/1994 | Klicek |
| 5,281,217 A | 1/1994 | Edwards et al. |
| 5,281,218 A | 1/1994 | Imran |
| 5,290,286 A | 3/1994 | Parins |
| 5,293,869 A | 3/1994 | Edwards et al. |
| 5,309,910 A | 5/1994 | Edwards et al. |
| 5,313,943 A | 5/1994 | Houser et al. |
| 5,314,466 A | 5/1994 | Stern et al. |
| 5,316,020 A | 5/1994 | Truffer |
| 5,328,467 A | 7/1994 | Edwards et al. |
| 5,334,196 A | 8/1994 | Scott et al. |
| 5,348,554 A | 9/1994 | Imran et al. |
| 5,363,861 A | 11/1994 | Edwards et al. |
| 5,365,926 A | 11/1994 | Desai |
| 5,365,945 A | 11/1994 | Halstrom |
| 5,366,490 A | 11/1994 | Edwards et al. |
| 5,368,557 A | 11/1994 | Nita et al. |
| 5,368,592 A | 11/1994 | Stern et al. |
| 5,370,675 A | 12/1994 | Edwards et al. |
| 5,370,678 A | 12/1994 | Edwards et al. |
| 5,383,876 A | 1/1995 | Nardella |
| 5,383,917 A | 1/1995 | Desai |
| 5,385,544 A | 1/1995 | Edwards et al. |
| 5,397,339 A | 3/1995 | Desai |
| 5,398,683 A | 3/1995 | Edwards et al. |
| 5,401,272 A | 3/1995 | Perkins |
| 5,403,311 A | 4/1995 | Abele et al. |
| 5,409,453 A | 4/1995 | Lundquist et al. |
| 5,421,819 A | 6/1995 | Edwards et al. |
| 5,423,808 A | 6/1995 | Edwards et al. |
| 5,423,811 A | 6/1995 | Imran et al. |
| 5,423,812 A | 6/1995 | Ellman et al. |
| 5,433,739 A | 7/1995 | Sluijter et al. |
| 5,435,805 A | 7/1995 | Edwards et al. |
| 5,441,499 A | 8/1995 | Fritzsch |
| 5,456,662 A | 10/1995 | Edwards et al. |
| 5,456,682 A | 10/1995 | Edwards et al. |
| 5,458,596 A | 10/1995 | Lax et al. |
| 5,458,597 A | 10/1995 | Edwards et al. |
| 5,470,308 A | 11/1995 | Edwards et al. |
| 5,471,982 A | 12/1995 | Edwards et al. |
| 5,472,441 A | 12/1995 | Edwards et al. |
| 5,484,400 A | 1/1996 | Edwards et al. |
| 5,486,161 A | 1/1996 | Lax et al. |
| 5,505,728 A | 4/1996 | Ellman et al. |
| 5,505,730 A | 4/1996 | Edwards |
| 5,507,743 A | 4/1996 | Edwards et al. |
| 5,509,419 A | 4/1996 | Edwards et al. |
| 5,514,130 A | 5/1996 | Baker |
| 5,514,131 A | 5/1996 | Edwards et al. |
| 5,520,684 A | 5/1996 | Imran |
| 5,531,676 A | 7/1996 | Edwards et al. |
| 5,531,677 A | 7/1996 | Lundquist et al. |
| 5,536,240 A | 7/1996 | Edwards et al. |
| 5,536,267 A | 7/1996 | Edwards et al. |
| 5,540,655 A | 7/1996 | Edwards et al. |
| 5,540,679 A * | 7/1996 | Fram et al. .................... 606/27 |
| 5,542,915 A | 8/1996 | Edwards et al. |
| 5,542,916 A | 8/1996 | Hirsch et al. |
| 5,545,161 A | 8/1996 | Imran |
| 5,545,171 A | 8/1996 | Sharkey et al. |
| 5,545,193 A | 8/1996 | Fleischman et al. |
| 5,545,434 A | 8/1996 | Huarng |
| 5,549,108 A | 8/1996 | Edwards et al. |
| 5,549,644 A | 8/1996 | Lundquist et al. |
| 5,554,110 A | 9/1996 | Edwards et al. |
| 5,556,377 A | 9/1996 | Rosen et al. |
| 5,558,672 A | 9/1996 | Edwards et al. |
| 5,558,673 A | 9/1996 | Edwards et al. |
| 5,562,720 A * | 10/1996 | Stern et al. .................... 607/98 |
| 5,599,345 A | 2/1997 | Edwards et al. |
| 5,607,422 A * | 3/1997 | Smeets et al. ................ 606/41 |
| 5,609,151 A | 3/1997 | Mulier et al. |
| 5,624,439 A | 4/1997 | Edwards et al. |
| 5,800,429 A * | 9/1998 | Edwards ....................... 606/41 |
| 5,800,482 A * | 9/1998 | Pomeranz et al. ........... 607/101 |
| 5,836,874 A * | 11/1998 | Swanson et al. ............. 600/374 |
| 5,860,974 A * | 1/1999 | Abele ........................... 606/41 |
| 6,063,079 A * | 5/2000 | Hovda et al. ................ 128/898 |
| 6,109,268 A * | 8/2000 | Thapliyal et al. ............ 128/898 |

FOREIGN PATENT DOCUMENTS

| | | |
|---|---|---|
| DE | 38 38 840 A | 2/1997 |
| EP | 0 139 607 A1 | 5/1985 |
| EP | 0 608 609 A2 | 8/1994 |
| WO | 92/10142 | 6/1992 |
| WO | 93/08755 | 5/1993 |
| WO | 94/10925 | 5/1994 |
| WO | 94/26178 | 11/1994 |
| WO | 95/18575 | 7/1995 |
| WO | 95/19142 | 7/1995 |
| WO | 95/25472 | 9/1995 |
| WO | 96/29946 | 10/1996 |

OTHER PUBLICATIONS

Mugica, et al., *Direct Diaphragm Stimulation,* Jan., 1987, PACE, vol. 10, pp. 252–256.

Mugica, et al., *Neurostimulation: An Overview,* Chapter 21, *Preliminary Test of a Muscular Diaphragm Pacing System on Human Patients* , 1985, pp. 263–279.

Nochomovitz, et al., *Electrical Activation of the Diaphragm,* Jun. 1988, Clinics in Chest Medicince, vol. 9, No. 2, pp.349–358.

Prior, et al., *Treatment of Menorrhagia by Radiofrequency Heating,*1991, Int. J. Hyperthermia, vol. 7, pp. 213–220.

Rice, et al., *Endoscopic Paranasal Sinus Surgery,* Chapter 5, *Functional Endoscopic Paranasal Sinus Surgery, The Technique of Messerklinger,*Raven Press, 1988, pp.75–104.

Rice, et al., *Endoscopic Paranasal Sinus Surgery*, Chapters 6, *Total Endoscopic Sphenoethmoidectomy, The Technique of Wigand,* Raven Press, 1988, pp.105–125.

* cited by examiner

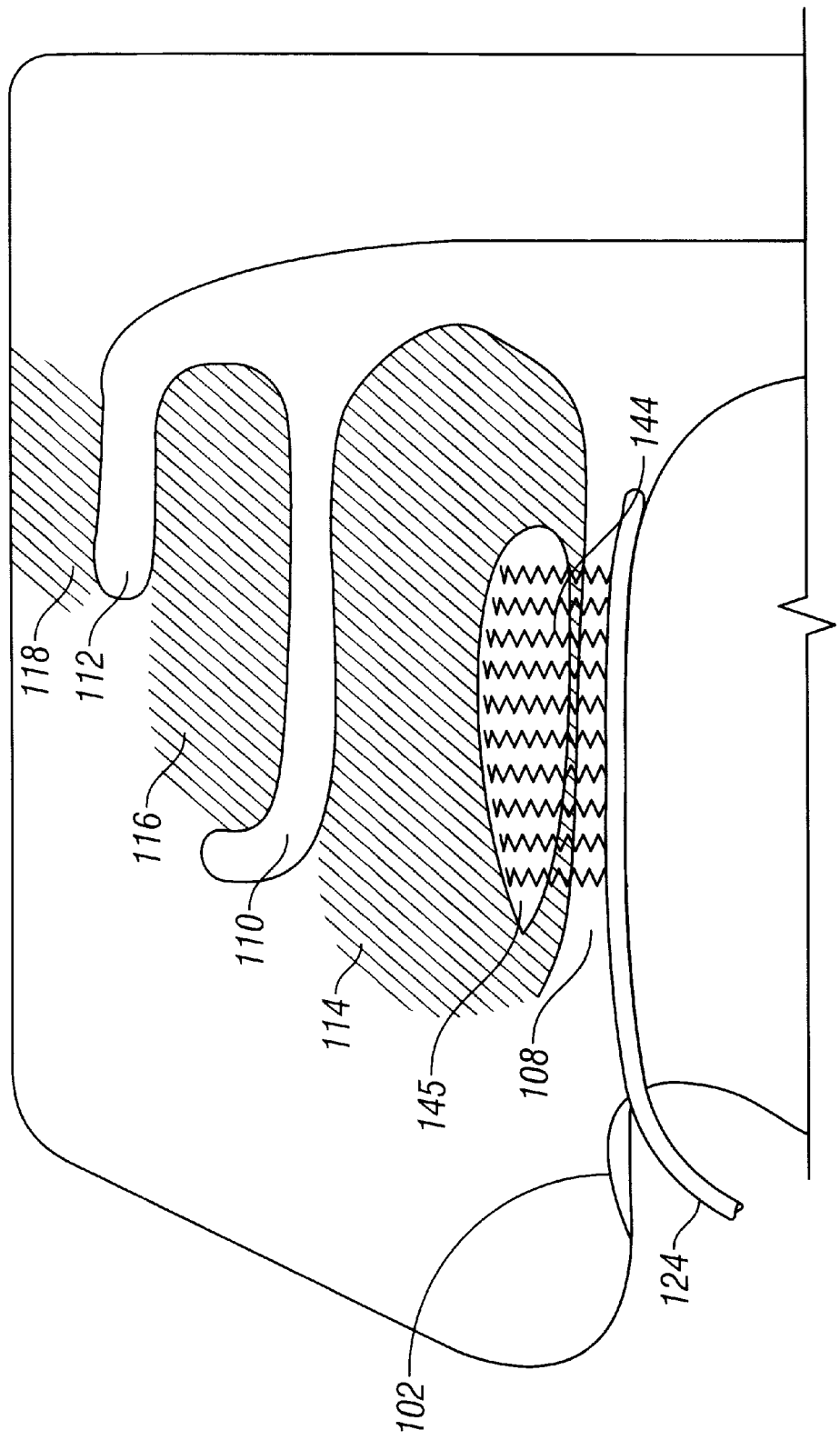

APPARATUS FOR ABLATING TURBINATES

This application is a continuation of application Ser. No. 08/753,063, "Apparatus for Ablating Turbinates", filed Nov. 19, 1996, now abandoned, which is a continuation-in-part of application Ser. No. 08/754,588, "Method for Ablating Turbinates", filed Nov. 19, 1996, now U.S. Pat. No. 5,746,224 and application Ser. No. 08/752,076, "Noninvasive Apparatus for Ablating Turbinates", filed Nov. 19, 1996, now U.S. Pat. No. 5,800,429, both of which are continuations-in-part of application Ser. No. 08/651,796, "Method and Apparatus for Ablating Turbinates" filed May 22, 1996 (now abandoned) and of application Ser. No. 08/651,798, "Method and Apparatus for Ablating Turbinates", filed May 22, 1996 (now abandoned); all of which are a continuation-in-part of application Ser. No. 08/265,459, "Thin Layer Ablation Apparatus", filed Jun. 24, 1994, now U.S. Pat. No. 5,505,730, all of which are incorporated herein by reference.

FIELD OF THE INVENTION

The present invention relates to a method and apparatus for treating airway obstructions. More specifically, the present invention relates to a method and apparatus for reducing the volume of the turbinates in order reduce nasal airway obstructions.

BACKGROUND OF THE INVENTION

Sleep-apnea syndrome is a medical condition characterized by daytime hypersomnomulence, morning arm aches, intellectual deterioration, cardiac arrhythmias, snoring and thrashing during sleep. It is caused by frequent episodes of apnea during the patient's sleep. The syndrome is classically subdivided into two types. One type, termed "central sleep apnea syndrome", is characterized by repeated loss of respiratory effort. The second type, termed obstructive sleep apnea syndrome, is characterized by repeated apneic episodes during sleep resulting from obstruction of the patient's upper airway or that portion of the patient's respiratory tract which is cephalad to, and does not include, the larynx.

Treatment thus far includes various medical, surgical and physical measures to unobstruct the airways. Medical measures include the use of medications such as protriptyline, medroxyprogesterone, acetazolamide, theophylline, nicotine and other medications in addition to avoidance of central nervous system depressants such as sedatives or alcohol. The medical measures above are sometimes helpful but are rarely completely effective. Further, the medications frequently have undesirable side effects.

Surgical interventions have included uvulopalatopharyngoplasty, tonsillectomy, surgery to correct severe retrognathia and tracheostomy. Other surgical procedures include pulling the tongue as forward as possible and surgically cutting and removing sections of the tongue and other structures which can close off the upper airway passage. These procedures may be effective but the risk of surgery in these patients can be prohibitive and the procedures are often unacceptable to the patients.

Among the air passageways in the body that can become obstructed are the nasal passageways leading from the nose to the pharynx. There are three nasal passageways, namely the inferior, middle and superior nasal meatus. The turbinates, also referred to as nasal concha, are a series of tissues which form at least a portion of these nasal passageways. Forming a portion of the inferior nasal meatus is the inferior nasal concha. The inferior and middle nasal concha each form a portion of the middle nasal meatus. The middle and superior nasal concha each form a portion of the superior nasal meatus. When the inferior, middle and/or superior nasal concha become enlarged, the various nasal meatus which allow air to pass through the nose into the pharynx can become obstructed.

Opening of obstructed nasal airways by reducing the size of the turbinates has been performed using surgical and pharmaceutical treatments. Examples of surgical procedures include anterior and posterior ethmoidectomy, such as those described in "Endoscopic Paranasal Sinus Surgery" by D. Rice and S. Schaefer, Raven Press, 1988); the writings of M. E. Wigand, Messerklinger and Stamberger; and U.S. Pat. No. 5,094,233. For example, as described in U.S. Pat. No. 5,094,233, the Wigand procedure involves the transection of the middle turbinate, beginning with the posterior aspect, visualization of the sphenoid ostium and opening of the posterior ethmoid cells for subsequent surgery. In the sphenoidectomy step, the ostium of the sphenoid is identified and the anterior wall of the sinus removed. Following this step, the posterior ethmoid cells may be entered at their junction with the sphenoid and the fovea ethmoidalis can be identified as an anatomical landmark for further dissection. In anterior ethmoidectomy, the exenteration of the ethmoids is carried anteriorly to the frontal recess. Complications, such as hemorrhage, infection, perforation of the fovea ethmoidalis or lamina papyracea, and scarring or adhesion of the middle turbinate, are reported in connection with these procedures.

A particular problem encountered has been postoperative adhesion occurring between the turbinates and adjacent nasal areas, such as medial adhesion to the septum and lateral adhesion to the lateral nasal wall in the area of the ethmoid sinuses. Otherwise successful surgical procedures may have poor results in these cases. Some surgeons have proposed amputation of a portion of the turbinate at the conclusion of surgery to avoid this complication, resulting in protracted morbidity (crust formation and nasal hygiene problems). The turbinate adhesion problem detracts from these endoscopic surgical procedures. Efforts have been made to reduce the complications associated with the surgical treatment of turbinate tissue, for example by the use of a turbinate sheath device. U.S. Pat. No. 5,094,233.

U.S. Pat. No. 3,901,241 teaches a cryosurgical instrument which is said to be useful for shrinking nasal turbinates. U.S. Pat. No. 3,901,241.

Pharmaceuticals have also been developed for reducing the size of the turbinates. However, pharmaceuticals are not always completely efficacious and generally do not provide a permanent reduction in turbinate size. In addition, pharmaceuticals can have adverse side effects.

A need exists for a method and device for clearing obstructed nasal passageways. It is preferred that the method and device be performable with minimal surgical intervention or post operative complications. It is also preferred that the method and device be performable so as to reduce the size of the turbinates without the surgical cutting or removal of tissue. It is also preferred that the method and device provide a permanent reduction in turbinate size.

SUMMARY OF THE INVENTION

An apparatus is provided for ablating at least a portion of a nasal concha. In one embodiment, the apparatus includes a catheter having a distal portion with a dimension configured for positioning the catheter distal portion through a nostril of a patient into a nasal meatus adjacent a surface of a nasal concha, an expandable member positioned at the catheter distal portion, an energy delivery device positioned at the catheter distal portion for delivering ablative energy to the surface of the nasal concha, and a lumen positioned within the catheter for delivering a medium into the expandable member to expand the expandable member.

The present invention also relates to an apparatus for ablating a selected portion of a nasal concha. In this embodiment, the apparatus includes a catheter having a distal portion with a dimension configured for positioning the catheter distal portion through a nostril of a patient into a nasal meatus adjacent a surface of a nasal concha, an energy delivery device for delivering ablative energy positioned at the catheter distal portion, and an insulator positioned to cause delivery of ablative energy to a selected portion of a nasal concha while insulating other tissue forming the nasal meatus from the ablative energy.

The present invention also relates to an apparatus for ablating an internal section of a nasal concha. According to this embodiment, the apparatus includes a catheter having a distal portion with a dimension configured for positioning the catheter distal portion through a nostril of a patient into a nasal meatus adjacent a surface of a nasal concha, an expandable member positioned at the catheter distal portion, an energy delivery device for delivering ablative energy positioned at the catheter distal portion, a lumen positioned within the catheter for delivering a medium into the expandable member to expand the expandable member to adjacent a surface of the nasal concha, and a medium source for delivering medium of a sufficiently low temperature to cool the surface of the nasal concha during energy delivery. According to this embodiment, the energy used should be of a type which can penetrate into an internal section of tissue and cause ablative heating therein. Examples of this type of energy included electromagnetic energy (RF, microwave) and ultrasonic.

BRIEF DESCRIPTION OF THE DRAWINGS

FIG. 3A illustrates the introduction of an apparatus through a nostril into a nasal meatus adjacent a surface of a nasal concha.

FIG. 3B illustrates the expansion of the expandable member within the nasal meatus so that the energy delivery device is brought into energy communication with the surface of the nasal concha to be treated.

FIG. 3C illustrates the delivery of energy to a selected portion of a nasal concha by selecting the placement of the apparatus within the nasal meatus.

FIG. 3D illustrates insulating at least a portion of the nasal concha from ablative energy.

FIGS. 4A–C illustrate the steps of ablating a portion of a nasal concha according to the present invention.

FIG. 4A illustrates the step of introducing ablative energy into an interior section of a nasal concha.

FIG. 4B illustrates an ablated tissue region and its absorption by the body.

FIG. 4C illustrates the resulting reduction in the size of the nasal concha.

DETAILED DESCRIPTION OF THE PREFERRED EMBODIMENT

The present invention provides a method and apparatus for ablating at least a portion of a nasal concha (turbinate). By ablating at least a portion of a nasal concha, the size of the nasal concha can be reduced. Accordingly, the present invention also provides a method for reducing the size of a nasal concha. The three nasal concha in the body (inferior, middle and superior nasal concha) form at least a portion of three nasal meatus (inferior, middle and superior nasal meatus) in the body. By reducing the size of a nasal concha, obstruction of a nasal meatus can be reduced. By reducing an obstruction of a nasal meatus, air flow through the nasal meatus is improved. Accordingly, the present invention also relates to a method for improving airflow through a nasal meatus of the body.

Figure 1:
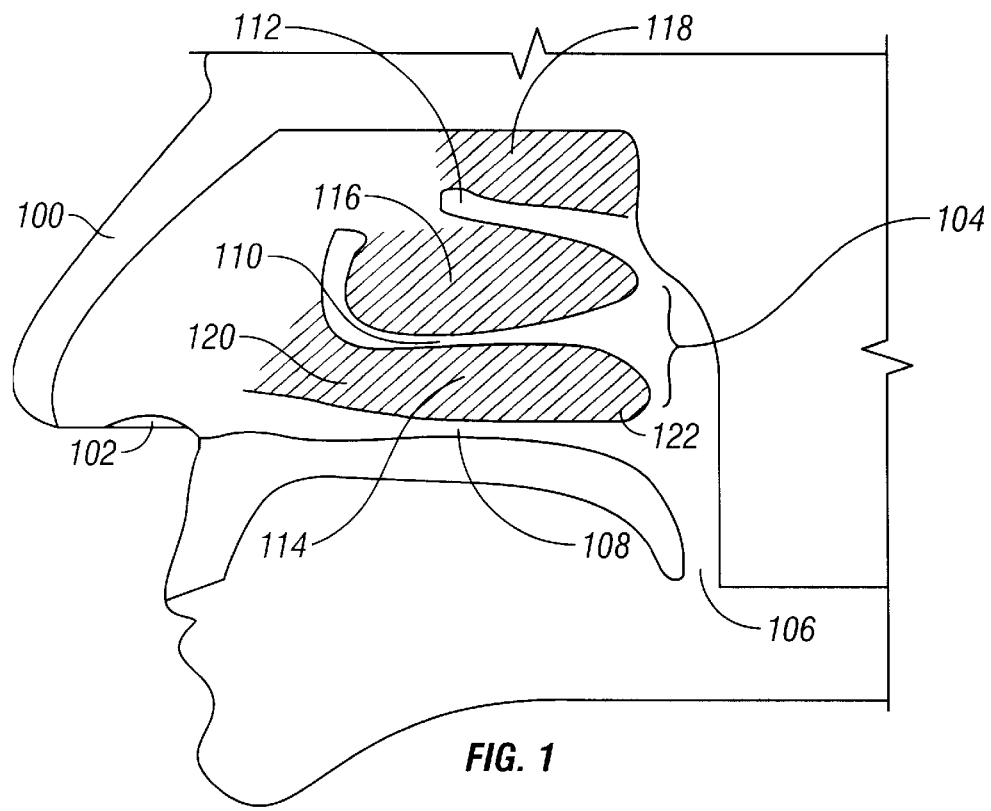
FIG. 1 illustrates the construction of the nasal passageways of the human nose.

FIG. 1 illustrates the construction of the nasal passageways of the human nose 100. As illustrated in the figure, the human nose includes a nostril 102 which leads into the nasal passageways from outside the body and a nasopharyngeal opening 104 which leads into the nasal passageways from the pharynx 106. Connecting the nostril 102 and nasopharyngeal opening 104 are a series of passageways, namely the inferior nasal meatus 108, the middle nasal meatus 110, and the superior nasal meatus 112. Forming at least a portion of each of these passageways are the nasal concha, also referred to as the turbinates. Forming at least a portion of the inferior nasal meatus 108 is the inferior nasal concha 114. Forming at least a portion of the middle nasal meatus 110 is the inferior nasal concha 114 and the middle nasal concha 116. Forming at least a portion of the superior nasal meatus 112 is the middle nasal concha 116 and the superior nasal concha 118. As also shown in FIG. 1, the inferior nasal concha 114 includes an anterior portion 120 which terminates adjacent the nasopharyngeal opening 104 and a posterior portion 122 which terminates adjacent the nostril 102.

Ablation of a nasal concha is accomplished according to the present invention by the introduction of ablative energy into a section of nasal concha tissue. The use of ablative energy eliminates the need for surgical cutting to remove a portion of a nasal concha and the risks associated therewith. As a result, the procedure can be performed bloodlessly and without the need to penetrate tissue, thereby significantly reducing the risk of infection. By cooling the surface of the nasal concha being ablated, ablation can be performed to remove an internal section of a nasal concha without damaging the surface of the nasal concha. As a result, the present invention provides a method for reducing the size of a nasal concha without the formation of a wound on the surface of the nasal concha. This approach should be significantly less painful for the patient than traditional surgical methods.

According to the present invention, it is preferred to ablate the inferior nasal concha 114, and more preferably an anterior portion 120 of the inferior nasal concha 114. In a preferred embodiment, the anterior portion 120 of the inferior nasal concha 114 is defined as being no larger than about one-third the volume of the inferior nasal concha 114. Thus, in one embodiment, the method includes ablating no more than about one-third of the inferior nasal concha 114.

Figure 2:
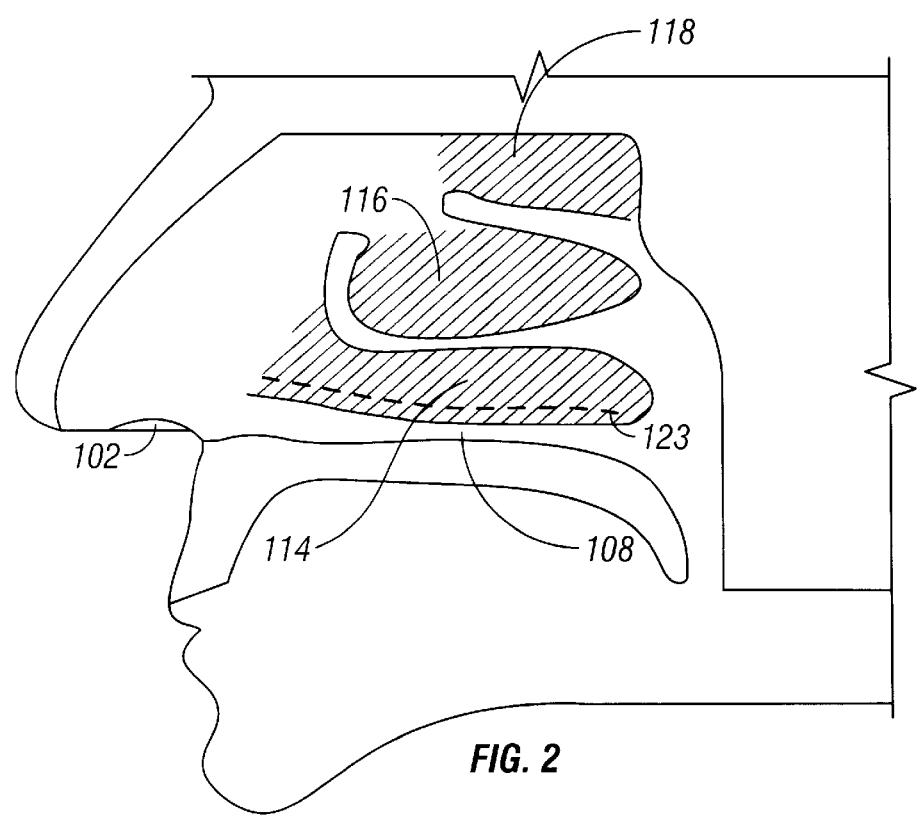
FIG. 2 illustrates the effect enlargement of a nasal concha has on a nasal air passageways.

FIG. 2 illustrates the effect enlargement of a nasal concha has on a nasal air passageways. As shown in FIG. 2, enlargement of the inferior nasal concha 114 can result in an obstruction of inferior nasal meatus 108. By reducing the size of the inferior nasal concha 114, illustrated in FIG. 2 by region below dashed line 123, the inferior nasal meatus 108 is reopened.

1. Method For Turbinate Ablation

Figure 3A:
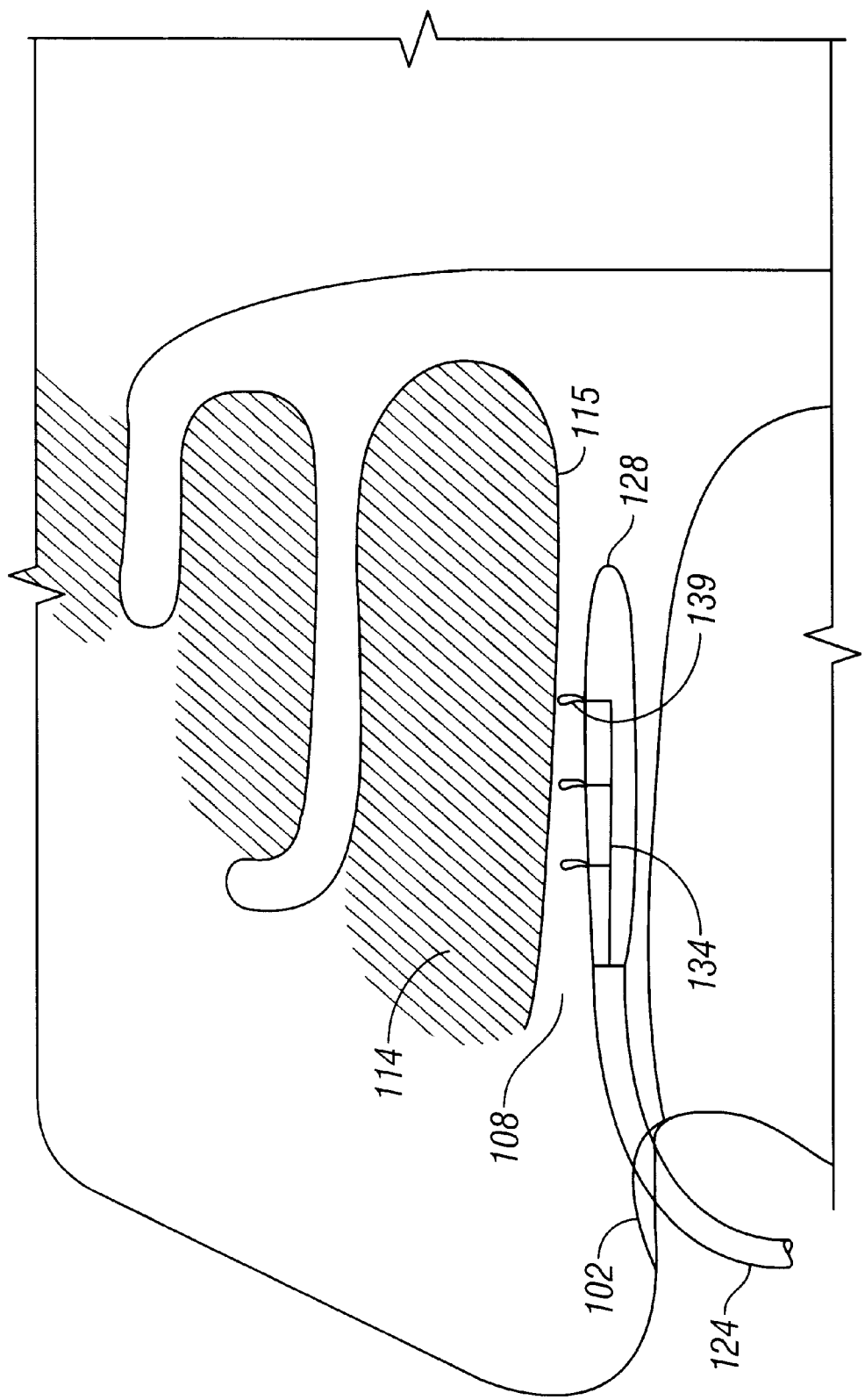
FIGS. 3A–3D illustrate an embodiment of a method for ablating a nasal concha.

One aspect of the present invention relates to a method for ablating nasal concha tissue. FIGS. 3A–3D illustrate an embodiment of this method. As shown in FIG. 3A, an apparatus 124 having a distal portion 128 with an expandable member 132 and an energy delivery device 134 for delivering ablative energy is introduced through a nostril 102 into a nasal meatus adjacent a surface of a nasal concha, shown in the figure as the inferior nasal meatus 108 and the inferior nasal concha 114.

Figure 3B:
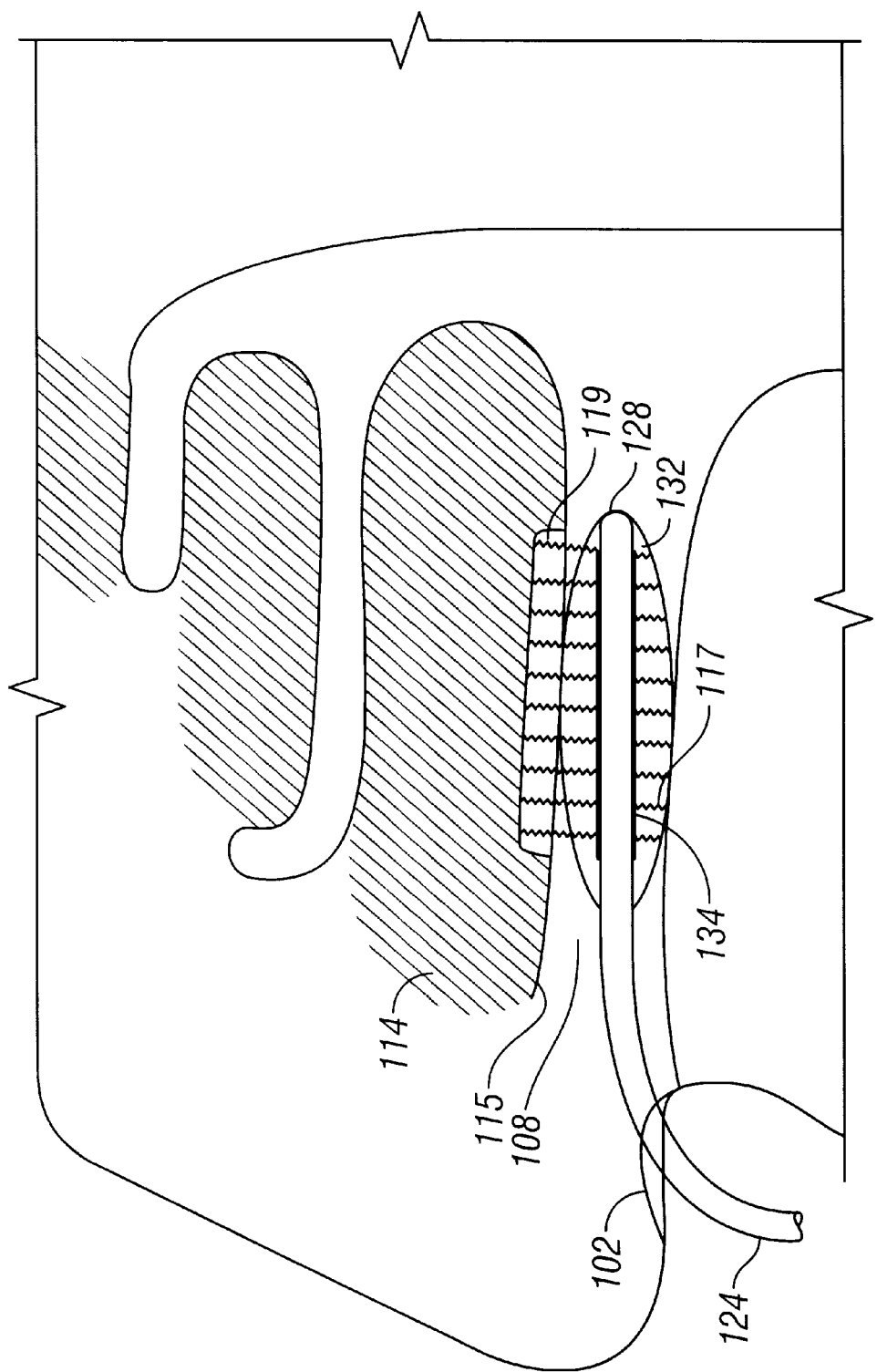

As shown in FIG. 3B, the expandable member 132 is expanded within the nasal meatus 108 so that the expandable member 132 is brought into contact with the surface 115 of the nasal concha 114 to be treated. Ablative energy 117 is then delivered through the apparatus and the energy delivery device 134 to the nasal concha 114. Sufficient energy 117 is delivered through the surface 115 of the nasal concha 114 to ablate at least a portion 119 of the nasal concha 114.

According to this method, the ablative energy may be any form of energy capable of causing the ablation of tissue by heating at least a portion of the nasal concha being treated to a temperature above about 40° C. Examples of types of energy that may be used include, but are not limited to energy from a diode laser ablation, a laser fiber (defused), microwave (915 MHz and 2.45 GHz), ultrasound, and RF at all relevant frequencies. In a preferred embodiment, the energy is electromagnetic energy and is preferably RF radiation or microwave radiation.

When the energy is RF radiation, the energy preferably has a frequency between about 300 megahertz and about 700 megahertz. The RF energy delivered to the nasal concha is preferably sufficient to deliver between about 5 and about 30 watts of RF energy to at least a portion of the nasal concha being treated.

Figure 3C:
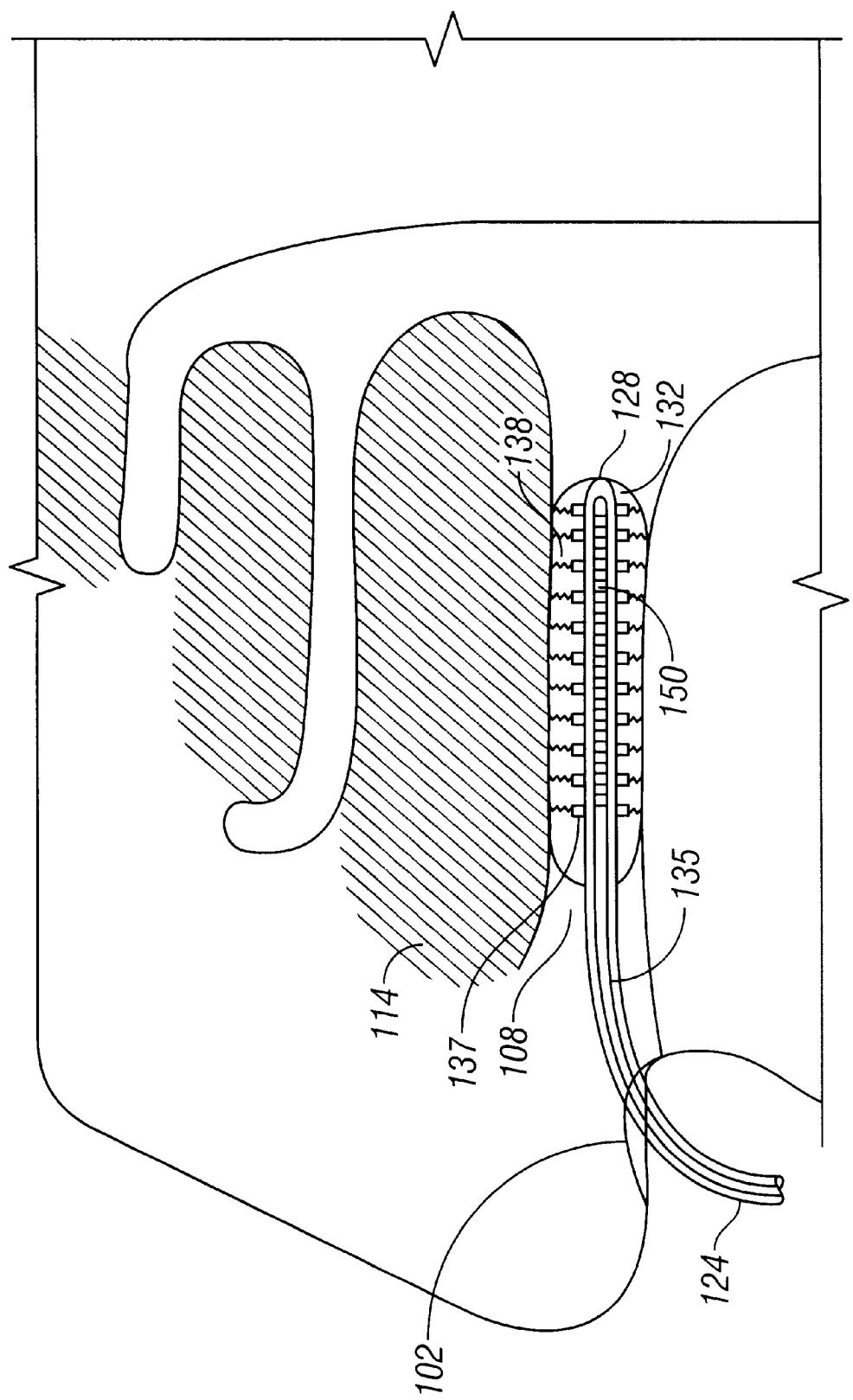

According to this method, the expandable member is preferably expanded by delivering a medium into the expandable member. FIG. 3C illustrates the delivery of the medium 138 through a lumen 135 within the distal portion of the apparatus into the expandable member 132 to expand the expandable member 132. The electrolytic medium 138 exits the lumen 135 through apertures 137 in the lumen wall. Accordingly, a further step of the method includes expanding the expandable member by delivering a medium into the member.

The medium may be any media capable of conducting energy from the energy delivery device to the nasal concha to be ablated. The medium can be a fluid or a gel. When RF energy is used, the medium is preferably a dielectric substance, such as saline, which aids the delivery of energy, referred to herein as an electrolytic medium. In one particular embodiment, the electrolytic medium is saline formed from distilled water with a NaCI content of less than about 10% by weight. The medium can also include a variety of substances known in the art for providing a bioactive, chemoactive, or radioactive effect desirable in conjunction with the ablation of turbinates. Examples of such substances include ablative acidic or alkaline substances, antibiotics, chemotherapeutic agents, a fluorescent or radioactive dye or marker, or some combination thereof.

In one embodiment of the method, the surface of the nasal concha to be ablated is cooled during the delivery of energy to ablate the nasal concha. The extent of cooling provided is preferably sufficient to prevent the nasal concha surface from being ablated. As a result, an interior portion of a nasal concha is ablated without ablating the surface of the nasal concha. In this regard, it is preferred that the cooling be sufficient to prevent the surface tissue from exceeding a temperature of about 40° C. In this embodiment, the energy used is of a type which can penetrate into an internal section of tissue despite surface cooling. Examples of this type of energy include electromagnetic energy and ultrasonic energy.

Cooling serves at least two purposes. Cooling may be used to prevent ablation of the surface of the nasal concha by preventing the ablation of the surface of the nasal concha. As a result, an exposed wound site is not generated during the method. Cooling may also be used to control the location of the ablation site. For example, cooling the nasal concha surface enables the formation of an entirely internal ablation site. The extent of cooling can be used to control the thickness of the non-ablated tissue at the surface of the nasal concha adjacent the internal ablation site.

Cooling may be accomplished, for example, by introducing cooled medium into the expandable member. Accordingly, the method may further include the step of introducing cooled medium into the expandable member during ablation.

The nasal meatus into which the apparatus is delivered may be the inferior, middle and/or superior nasal meatus and is preferably the inferior nasal meatus. The nasal concha ablated may be the inferior, middle and/or superior nasal concha and is preferably the inferior nasal concha. In one embodiment, energy is delivered to a selected section of one of the nasal concha. For example, energy may be selectively delivered to the anterior or posterior sections of the inferior nasal concha. Delivery of energy to a selected section of a nasal concha may be accomplished by the placement of the apparatus within the nasal meatus. The delivery of energy to a selected section of a nasal concha may also be accomplished by insulating at least a portion of the nasal concha from ablative energy.

Figure 3D:
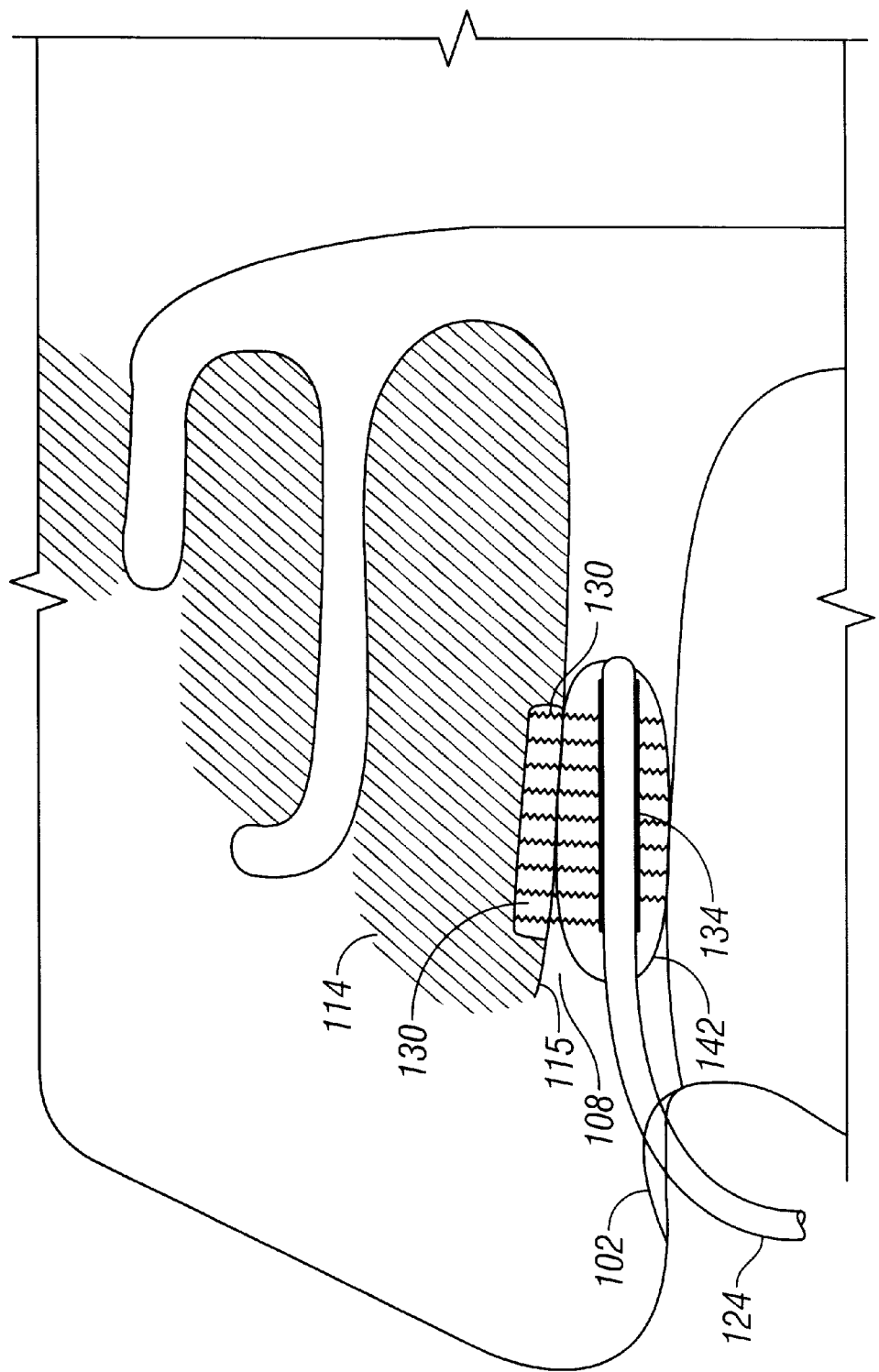

As illustrated in FIG. 3D, an insulative covering 142 may be positioned over a portion of the expandable member 132 to control the delivery of energy to a selected section of tissue. Accordingly, a further step of the method includes delivering energy to at least a portion of a nasal concha while insulating at least a portion of the tissue forming the nasal meatus from the energy being delivered to the nasal concha.

The present invention also relates to a method for reducing the size of a nasal concha. According to the method, the size of a nasal concha is reduced by ablating tissue forming a nasal concha and removing the ablated nasal concha tissue. Removal of the ablated nasal concha tissue is preferably accomplished by the natural absorption of ablated tissue by the patient's body.

Figure 4B:
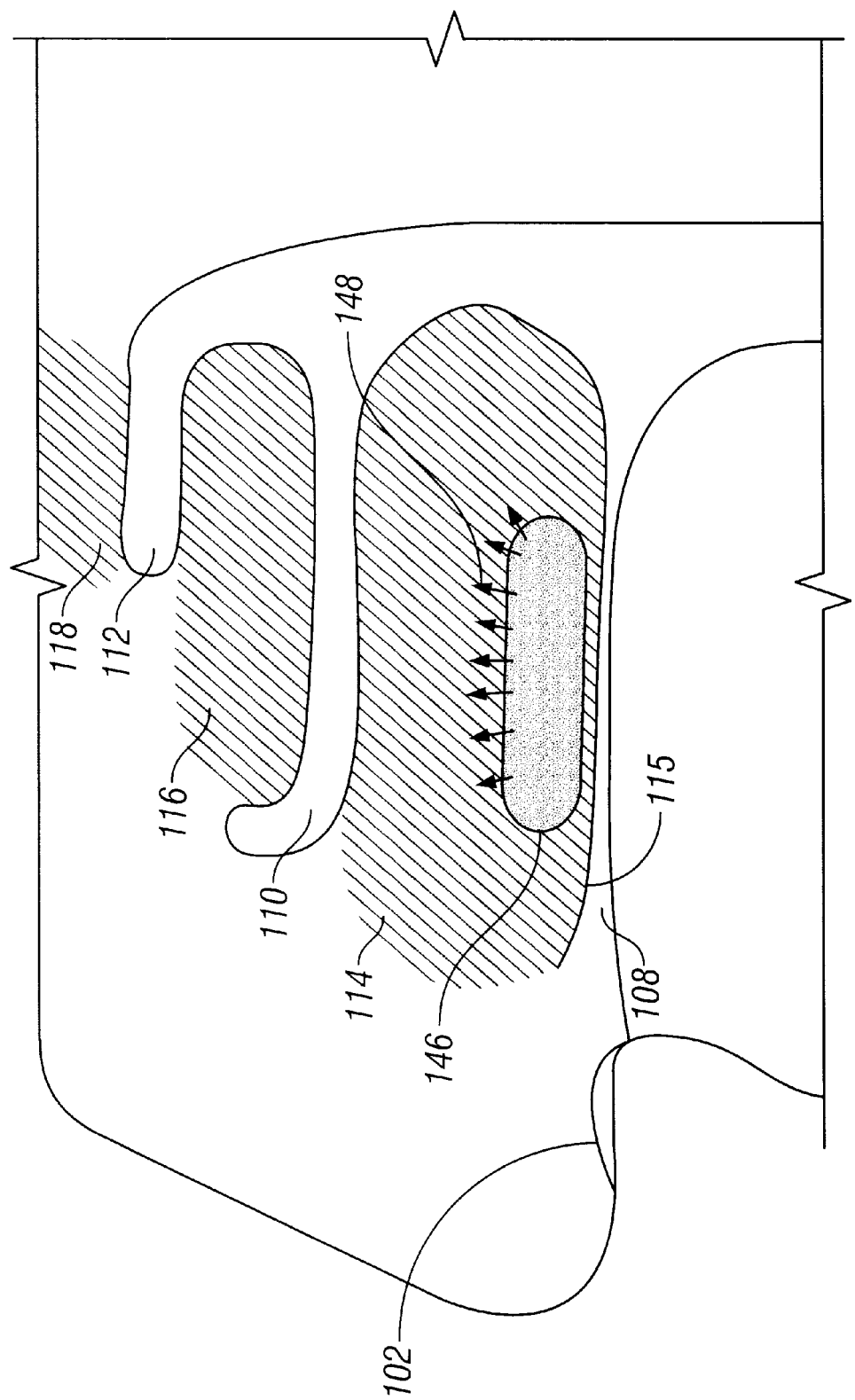
Figure 4C:
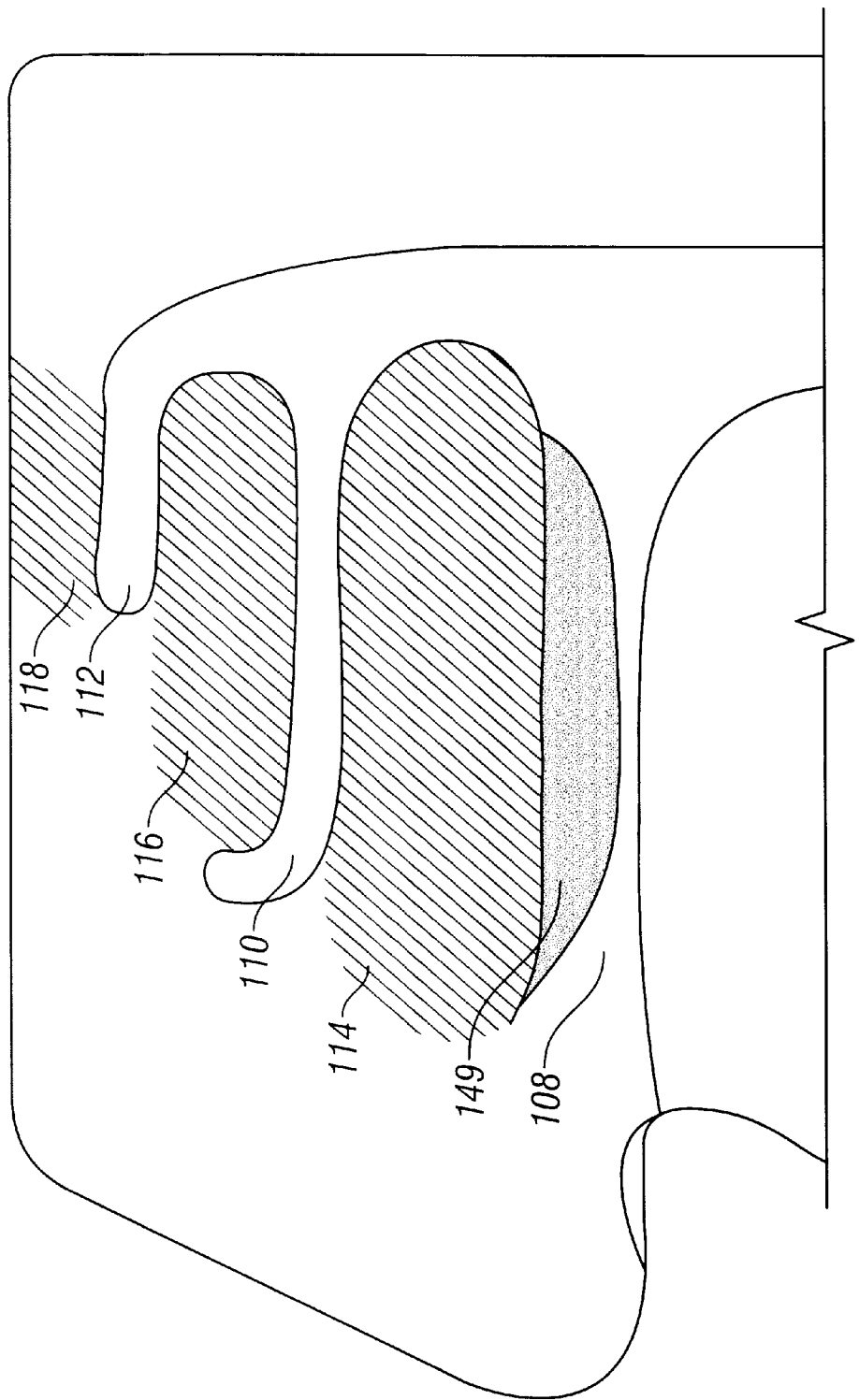

FIGS. 4A–C illustrate the removal of an internal region of tissue by ablation. FIG. 4A illustrates introducing ablative energy 144 into an interior section of a nasal concha through the surface of the nasal concha. Cooling of the surface of the nasal concha may be performed in order to prevent the ablation of the surface of the nasal concha.

FIG. 4B illustrates the absorption (illustrated by arrows 148) of an ablated tissue region 146 by the body. As illustrated in FIG. 4B, the ablated tissue region 146 is an interior region, i.e., the surface 115 of the nasal concha has not been ablated. This may be achieved by cooling the surface 115 of the nasal concha during the delivery of ablative energy to the nasal concha.

FIG. 4C illustrates the resulting reduction in the size of the nasal concha after absorption. Region 149 illustrates the volume of tissue that is removed from the path of the nasal meatus by this method. As can be seen by comparing FIGS. 4A and 4C, the size of nasal meatus 108 is enlarged by this process.

The present invention also relates to a method for improving airflow through a nasal meatus by reducing the size of a nasal concha which defines at least a portion of the nasal meatus. This method can be accomplished by the method for reducing the size of a nasal concha as described above. In one embodiment, the rate of airflow through the nasal meatus at a given pressure is increased by at least 25%.

2. Turbinate Ablation Apparatus

Figure 5:
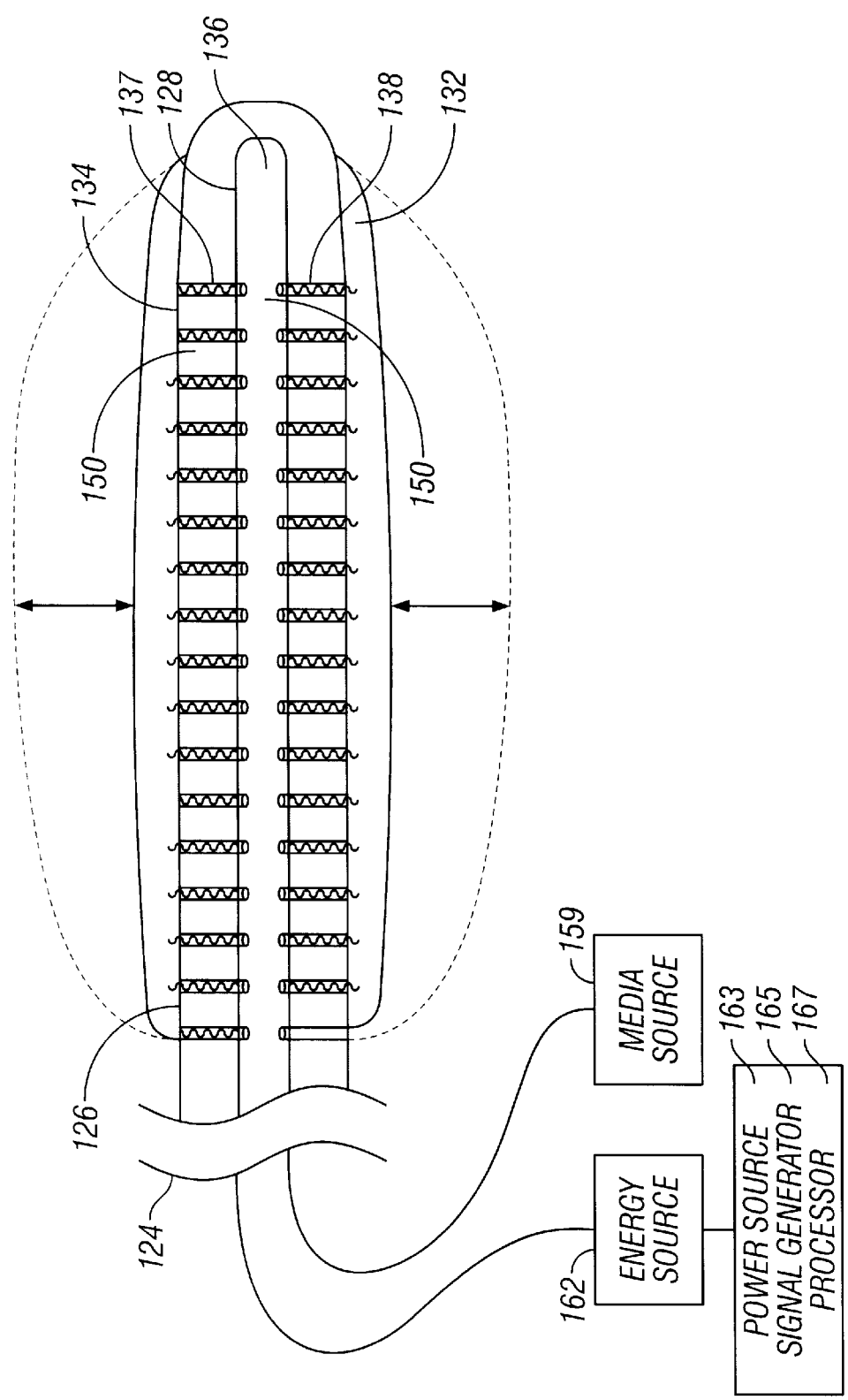
FIG. 5 illustrates an apparatus according to the present invention.

The present invention also relates to an apparatus for ablating a nasal concha. As illustrated in FIG. 5, the apparatus 124 includes a catheter body 126 which has a distal portion 128 with dimensions configured for introduction through a nostril of a patient into a nasal meatus of a patient.

An expandable member 132 is attached to the catheter body 126 at the catheter distal portion 128. Also attached to the catheter body 126 at the catheter distal portion 128 is an energy delivery device 134 for delivering ablative energy.

According to the present invention, the expandable member preferably conforms to the surface of the nasal concha to be ablated when the expandable member is expanded. A variety of mechanisms known in the art may be used to expand the expandable member. One mechanism, illustrated in FIG. 5, involves the use of a lumen 136 coupled with the catheter body 126 for delivering a medium 138 to expand the expandable member 132. The medium is delivered from a media source 159 through the lumen 136 to within the expandable member 132 through apertures 137. The apertures 137 may be formed by a sheath 150 which substantially surrounds the lumen 136. In one embodiment, the sheath 150 is formed of a relatively inert and relatively hard substance, such as metallic copper or metallic silver. In alternative embodiments, the sheath 150 includes some other inert substance, such as gold, stainless steel, titanium, various plastic compounds, or some combination thereof.

The sheath preferably has a traverse diameter of about 6 french. (about 0.090 inches). However, it should be understood that the sheath may have a variety of thicknesses. The sheath 150 also preferably has a thickness of about 0.001 inches. This embodiment is particularly preferred in the case when the sheath is copper.

The medium used to expand the expandable member is preferably an electrolytic medium, i.e., a medium which is capable of conducting electromagnetic energy and can be used to convey energy from the energy delivery device to the nasal concha to be ablated.

The expandable member is preferably formed of a material which is permeable to the electrolytic medium used to expand the member. By selecting the material used to form the expandable member such that it is permeable to the electrolytic medium, the electrolytic medium is able to pass through the expandable member to the surface of the nasal concha being ablated during operation of the apparatus. In one embodiment, the expandable member is an expandable porous membrane.

As illustrated in FIG. 5, the energy delivery device 134 may be positioned within the expandable member. This energy delivery device may be a needle electrode or a conductive film lining the outside of the lumen. The sheath may also serve as the energy delivery device. Alternatively, the energy delivery device may be positioned on a surface 147 of the expandable member. The energy delivery device may be a single energy delivery device or may include a plurality of energy delivery devices where energy is independently deliverable to each energy delivery device.

Figure 6:
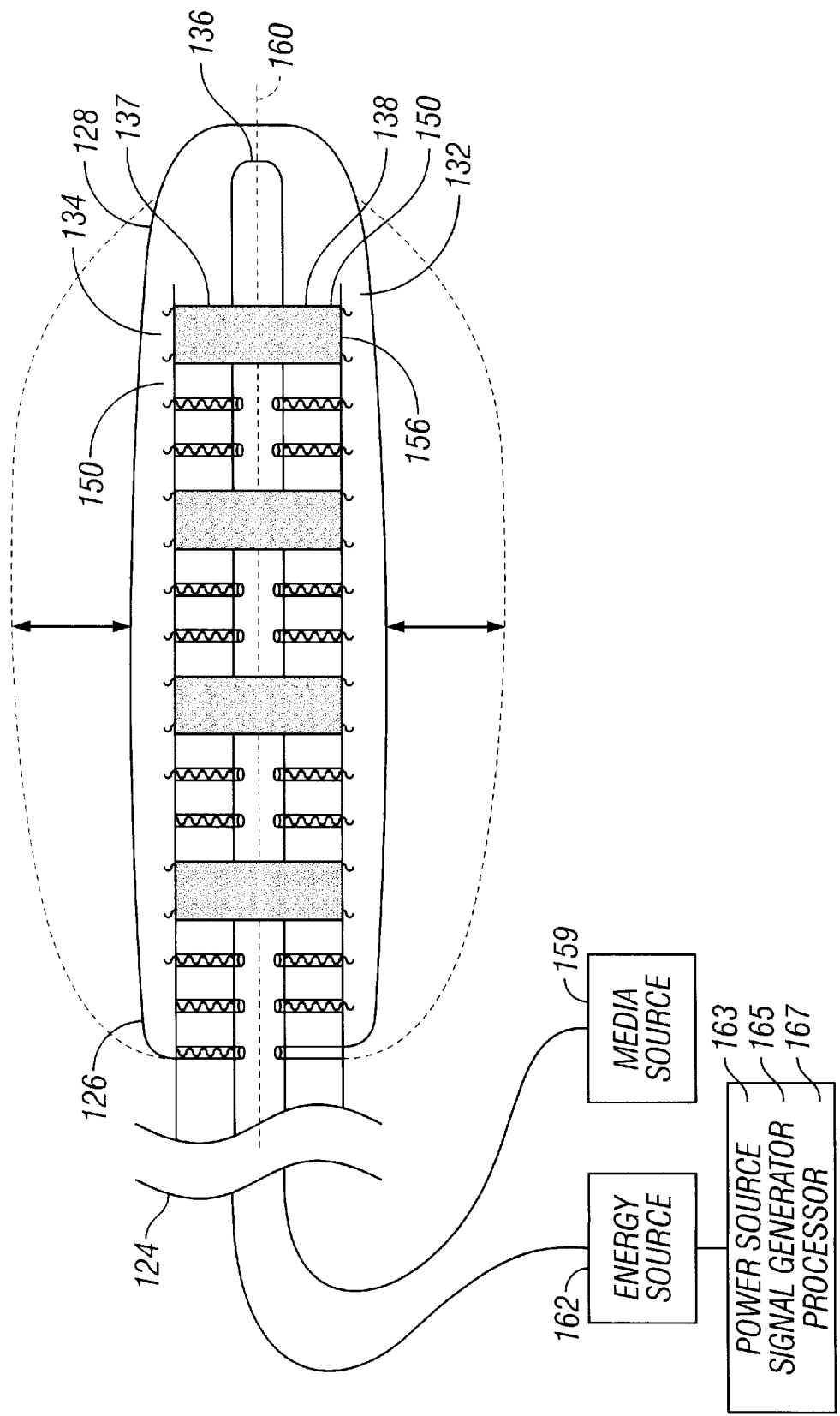
FIG. 6 illustrates the use of a plurality of ring electrodes in an apparatus according to the present invention.

In one embodiment, illustrated in FIG. 6, the energy delivery device includes one or more ring electrodes 156 disposed on the surface of the expandable member 132. As illustrated, the plurality of ring electrodes 156 may be disposed in parallel with their axes aligned with a long axis 160 of the catheter body 126. As noted above, energy may be delivered to all of the energy delivery devices or may be independently delivered to each energy delivery device.

In another embodiment, a plurality of energy delivery devices are positioned on a surface of the expandable member. An example of a suitable surface for disposition on the membrane is described in application Ser. No. 08/319, 373, "Thin Layer Ablation Apparatus", filed Oct. 6, 1994, which is incorporated by reference. It is noted that a combination of ring electrodes and surface energy delivery devices may be used.

Figure 7:
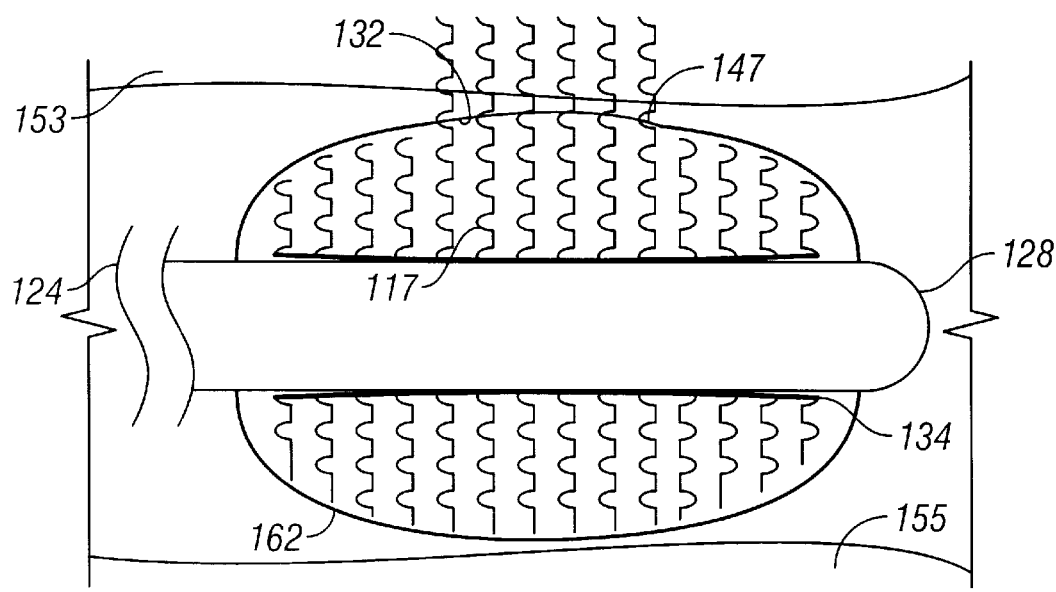
FIG. 7 illustrates an apparatus which includes an insulator for selectively delivering ablative energy to a desired section of a nasal concha.

In a further embodiment of the invention, illustrated in FIG. 7, the apparatus includes an insulator 162 which prevents the delivery of ablative energy 117 through at least a portion of the expandable member. As illustrated in FIG. 7, the insulator 162 may be positioned over the surface 147 of the expandable member 132. Using the insulator 162, ablative energy can be delivered to a selected section of a nasal concha 153 while preventing the ablation of another selected section of tissue 155. For example, ablative energy can be selectively delivered to a nasal concha forming at least a portion of the nasal meatus. Meanwhile, the insulator can be used to prevent the ablation of other portions of the nasal meatus.

As illustrated in FIG. 5, ablative energy is supplied to the energy delivery device by an energy source 162. As discussed above, a variety of forms of ablative energy may be used in the present invention. Accordingly, the energy source is selected to provide the desired form of energy. The energy used is preferably RF energy which ablates the turbinate by heat and cell destruction.

In one embodiment, the energy source 162 includes an energy source 163 (or a power regulator coupled to a standard energy source such as a wall socket or battery), a signal generator 165 (such as a generator for pulses, sine waves, square waves, or some combination of these wave forms with each other or with some other wave form), and a processor 167 for controlling the signal generator.

In a preferred embodiment, the signal generator generates pulses of RF energy having an RF radiation frequency between about 300 megahertz and about 700 megahertz, such as preferably about 465 megahertz. In alternative embodiments, the RF energy may have an RF radiation frequency in the microwave range or in another range of the electromagnetic spectrum.

The processor controls the amount of energy delivered by the apparatus. In this embodiment, the apparatus can further include a signal generator coupled to the energy delivery device and coupled to a energy source. The apparatus can also include a processor coupled to the signal generator and disposed for controlling the signal generator. According to this embodiment, the processor can control the way in which energy is delivered. For example, the signal generator can generate pulses of RF energy which provide between about 5 and about 30 watts of RF energy to at least a portion of the turbinate. The processor can also control the amount of energy produced so that the region of turbinate tissue to be ablated is heated to a temperature of at least 40° C.

In order to monitor the amount of energy delivered and the amount of heat generated, the apparatus can also include one or more sensors. These sensors can be used to detect a variety of operating parameters including the amount of energy delivered, the impedance generated, and the temperature of a region adjacent the apparatus. These sensors can also be used to provide feedback for controlling the operation of an energy source which delivers energy to the energy delivery device. In addition, chemical or biochemical sensors can be used to detect ablation.

In one embodiment, the apparatus includes at least one temperature sensor, such as a thermocouple or thermistor. The temperature sensor is coupled to a communication link (such as a conductor), which is coupled to the processor. For example, in the case where the temperature sensor is a thermocouple, the communication link may comprise a D/A converter coupled to a register disposed for reading by the processor. The processor reads an sensor value from the sensor and, responsive thereto, controls the signal generator so as to achieve delivery of an effective amount of RF energy to a desired section of tissue to be ablated. The processor thus uses the signal generator, catheter distal portion, energy delivery device, and temperature sensor, as a feedback loop for controlled delivery of RF energy to a section of a nasal concha. For example, the processor may control the delivery of RF energy to achieve delivery of a selected amount of energy, to achieve a selected temperature, or to achieve a selected amount of ablation of a section of a nasal concha. A variety of positionings for the sensors are possible. In one embodiment, the sensor is coupled to the expandable member.

Figure 8:
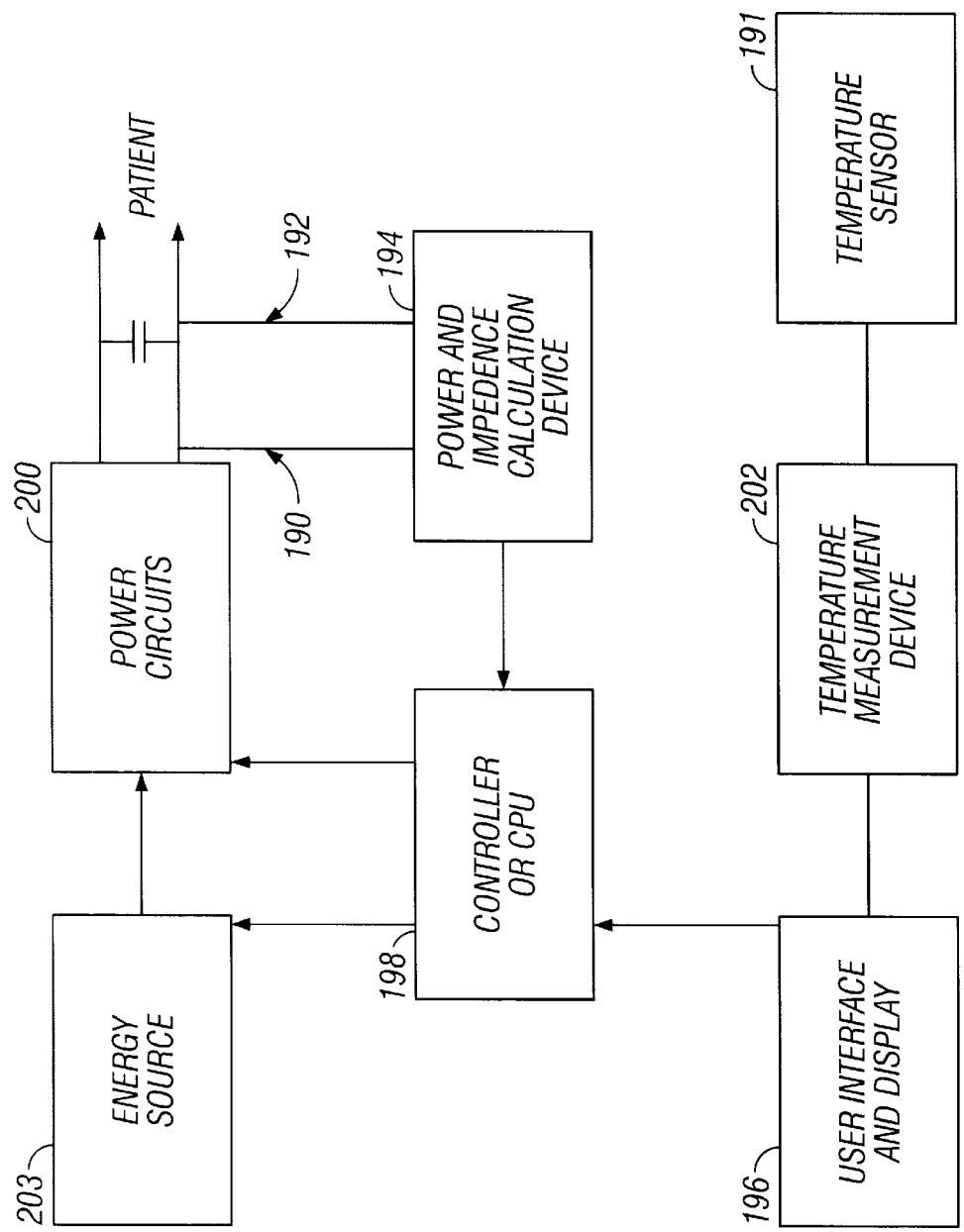
FIG. 8 is a block diagram of a feedback control system useful with the method and apparatus of the present invention.
Figure 9:
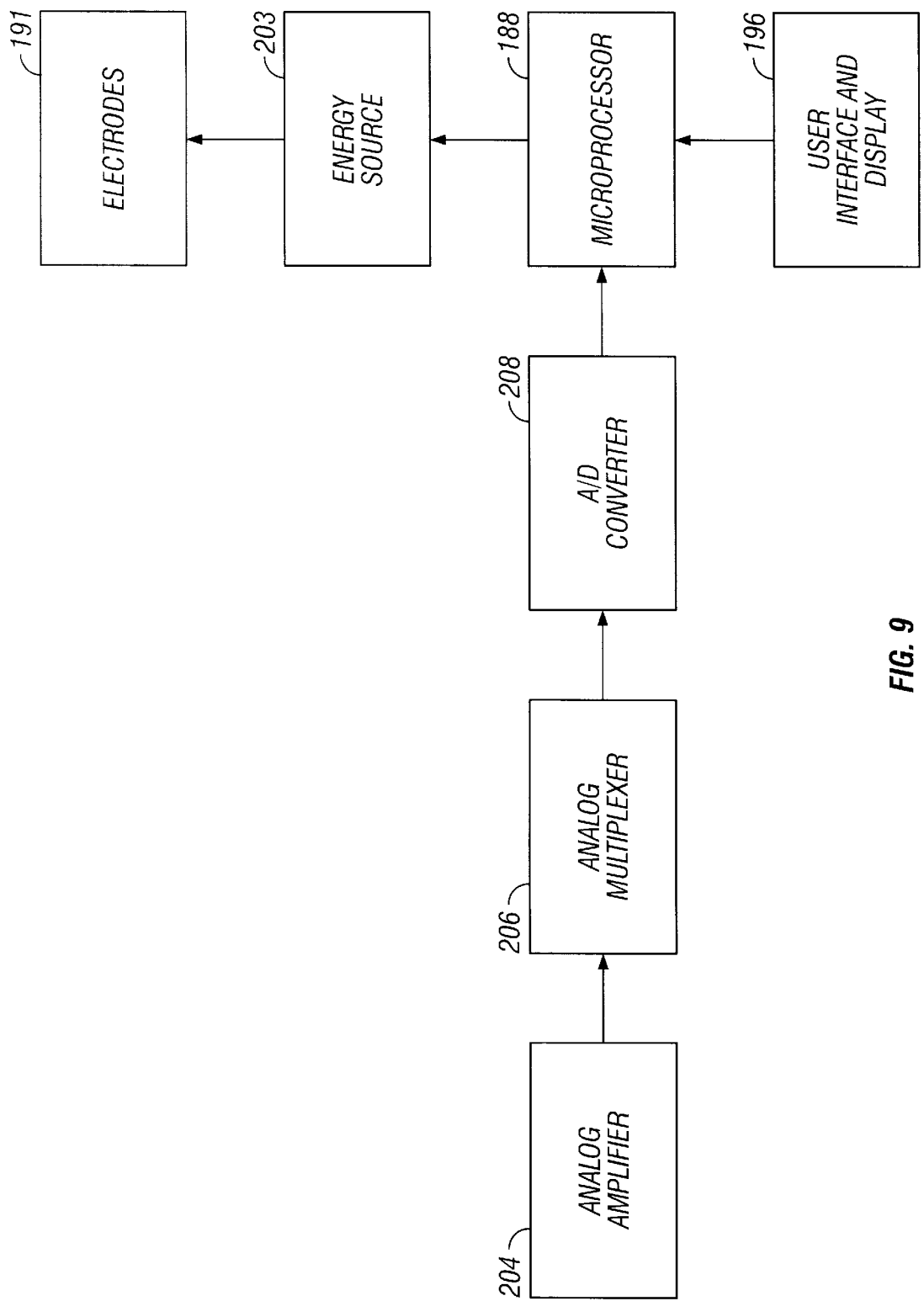
FIG. 9 is a block diagram illustrating an analog amplifier, analog multiplexer and microprocessor used with the feedback control system of FIG. 8.

As described above, the temperature or some other property of the tissue being ablated, or of the energy delivery device can be monitored using a variety of sensors. Illustrated in FIGS. 8 and 9 is an open and a closed loop feedback system for coupling a sensor used in the apparatus to an energy source so that the output energy of the energy source is adjusted in relation to the property sensed by the sensor. The feedback system, is described herein with regard to the delivery of RF energy. It should be noted, however, that the feedback system can be readily adjusted for use with a variety of other types of energy, such as microwaves.

Using the feedback system, the physician can, if desired, override the closed or open loop system. A microprocessor can be included and incorporated in the closed or open loop system to switch energy on and off, as well as modulate the energy. The closed loop system utilizes a microprocessor to serve as a controller, watch the temperature, adjust the amount of energy being delivered, look at the result, re-feed the result, and then modulate the energy.

In the case of RF energy, the sensors and feedback control system can be used to, maintained tissue adjacent to an energy delivery device at a desired temperature for a selected period of time without impeding out. An output maintains the energy delivered to the energy delivery device for a selected length of time.

As illustrated in FIG. 8, current is delivered through energy delivery device 189 is measured by current sensor 190. Voltage is measured by voltage sensor 192. Impedance and energy are then calculated at energy and impedance calculation device 194. These values can then be displayed at a user interface and display 196. Signals representative of energy and impedance values are received by a controller 198.

A control signal is generated by controller 198 that is proportional to the difference between an actual measured value, and a desired value. The control signal is used by energy circuits 200 to adjust the energy output in an appropriate amount in order to maintain the desired energy delivered at each energy delivery device 189.

In a similar manner, temperatures detected at temperature sensors 191 provide feedback for maintaining a selected energy. The actual temperatures are measured at temperature measurement device 202, and the temperatures are displayed at user interface and display 196. A control signal is generated by controller 198 that is proportional to the difference between an actual measured temperature, and a desired temperature. The control signal is used by energy circuits 200 to adjust the energy output in an appropriate amount in order to maintain the desired temperature delivered at the respective sensor. A multiplexer can be included to measure current, voltage and temperature, at numerous sensors, and energy can be delivered to the energy delivery device 189 in monopolar or bipolar fashion.

Controller 198 can be a digital or analog controller, or a computer with software. When controller 198 is a computer it can include a CPU coupled through a system bus. On this system can be a keyboard, a disk drive, or other non-volatile memory systems, a display, and other peripherals, as are known in the art. Also coupled to the bus is a program memory and a data memory.

User interface and display 196 includes operator controls and a display. Controller 198 can be coupled to imaging systems, including but not limited to ultrasound, CT scanners, X-ray, MRI, mammographic X-ray and the like. Further, direct visualization and tactile imaging can be utilized.

The output of current sensor 190 and voltage sensor 192 is used by controller 198 to maintain a selected energy level at energy delivery device 189. The amount of energy delivered controls the amount of energy. A profile of energy delivered can be incorporated in controller 198, and a preset amount of energy to be delivered can also be profiled.

Circuitry, software and feedback to controller 198 result in process control, and the maintenance of the selected energy that is independent of changes in voltage or current, and are used to change, (i) the selected energy, (ii) the duty cycle (on-off and wattage), (iii) bipolar or monopolar energy delivery, and (iv) infusion medium delivery, including flow rate and pressure. These process variables are controlled and varied, while maintaining the desired delivery of energy independent of changes in voltage or current, based on temperatures monitored at sensors 191.

Current sensor 190 and voltage sensor 192 are connected to the input of an analog amplifier 204. Analog amplifier 204 can be a conventional differential amplifier circuit for use with temperature sensors 191. The output of analog amplifier 204 is sequentially connected by an analog multiplexer 206 to the input of A/D converter 208. The output of analog amplifier 204 is a voltage which represents the respective sensed temperatures. Digitized amplifier output voltages are supplied by A/D converter 208 to microprocessor 188. Microprocessor 188 may be a type 68HCII available from Motorola. However, it will be appreciated that any suitable microprocessor or general purpose digital or analog computer can be used to calculate impedance or temperature.

Microprocessor 188 sequentially receives and stores digital representations of impedance and temperature. Each digital value received by microprocessor 188 corresponds to different temperatures and impedances.

Calculated energy and impedance values can be indicated on user interface and display 196. Alternatively, or in addition to the numerical indication of energy or impedance, calculated impedance and energy values can be compared by microprocessor 188 with energy and impedance limits. When the values exceed predetermined energy or impedance values, a warning can be given on user interface and display 196, and additionally, the delivery of RF energy can be reduced, modified or interrupted. A control signal from microprocessor 188 can modify the energy level supplied by energy source 203

Figure 10:
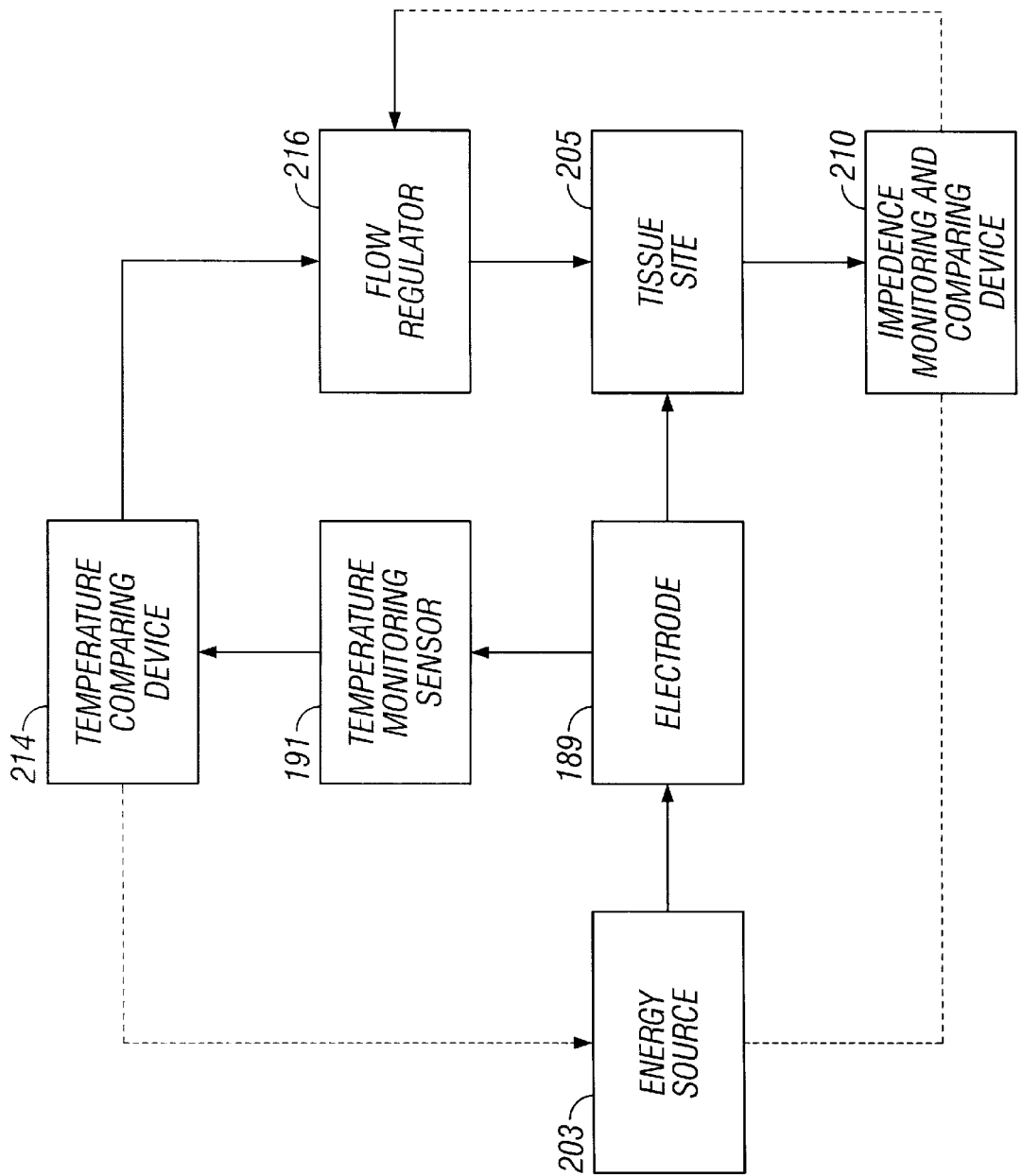
FIG. 10 is a block diagram of a temperature/impedance feedback system that can be used to control cooling medium flow rate through an apparatus of the present invention.

FIG. 10 illustrates a block diagram of a temperature/impedance feedback system that can be used to control cooling medium flow rate through the catheter into the expandable member. Ablative energy is delivered to energy delivery device 189 by energy source 203, and applied to tissue. A monitor 210 ascertains tissue impedance, based on the energy delivered to tissue, and compares the measured impedance value to a set value. If the measured impedance exceeds the set value a disabling signal 211 is transmitted to energy source 203, ceasing further delivery of energy to the energy delivery device 189. If measured impedance is within acceptable limits, energy continues to be applied to the tissue. During the application of energy to tissue sensor 191 measures the temperature of tissue and/or energy delivery device 189. A comparator 214 receives a signal representative of the measured temperature and compares this value to a pre-set signal representative of the desired temperature. Comparator 214 sends a signal to a flow regulator 216 representing a need for a higher cooling medium flow rate, if the tissue temperature is too high, or to maintain the flow rate if the temperature has not exceeded the desired temperature.

While the present invention is disclosed by reference to the preferred embodiments and examples detailed above, it is to be understood that these examples are intended in an illustrative rather than limiting sense, as it is contemplated that modifications will readily occur to those skilled in the art, which modifications will be within the spirit of the invention and the scope of the appended claims.

What is claimed is:

1. A method for ablating at least a portion of a nasal concha comprising:

introducing a distal portion of a catheter through a nostril and a nasal passageway, wherein the distal portion of the catheter includes at least a first RF electrode;

positioning the distal portion of the catheter adjacent to a portion of the nasal concha;

controllably delivering energy from the at least a first RF electrode to the nasal concha; and creating a sufficient ablation zone so as to reduce the size of the nasal concha.

2. The method of claim 1, wherein the distal portion includes at least a second RF electrode, and the at least first and second RF electrodes are bi-polar electrodes.

3. The method of claim 2, further comprising:

introducing an electrolytic solution to the at least the first RF electrode.

4. The method of claim 1, further comprising:

maneuvering the distal portion of the catheter as it is introduced through the nasal passageway to a position the distal portion adjacent to the inferior nasal concha.

5. The method of claim 1, wherein the distal portion of the catheter is dimensioned to be positioned into a nasal meatus adjacent a surface of a nasal concha.

6. The method of claim 1, wherein the size of the ablation zone is sufficient to improve air flow through a nasal meatus.

7. The method of claim 1, wherein the at least one RF electrode delivers energy at a frequency between about 300 megahertz and about 700 megahertz.

8. The method of claim 1, wherein the at least one RF electrode delivers about 5 to 30 watts of RF energy to at least a portion of the nasal concha.

9. The method of claim 1, wherein the size of the ablation zone is sufficient to increase a rate of airflow through a nasal meatus by at least 25%.

10. The method of claim 1, further comprising:

monitoring the delivery of energy from the at least one RF electrode through the surface of the nasal concha to the nasal concha.

* * * * *